(12) United States Patent  
Morita

(10) Patent No.: US 9,504,401 B2  
(45) Date of Patent: Nov. 29, 2016

(54) ATRIAL FIBRILLATION ANALYZER AND PROGRAM

(71) Applicant: Seiko Epson Corporation, Tokyo (JP)

(72) Inventor: Masanori Morita, Fussa (JP)

(73) Assignee: Seiko Epson Corporation, Tokyo (JP)

( * ) Notice: Subject to any disclaimer, the term of this patent is extended or adjusted under 35 U.S.C. 154(b) by 18 days.

(21) Appl. No.: 14/199,791

(22) Filed: Mar. 6, 2014

(65) Prior Publication Data

US 2014/0257124 A1 Sep. 11, 2014

(30) Foreign Application Priority Data

Mar. 7, 2013 (JP) ................................. 2013-045572

(51) Int. Cl.
*A61B 5/046* (2006.01)
*A61B 5/0456* (2006.01)
*A61B 5/11* (2006.01)

(52) U.S. Cl.
CPC ............ *A61B 5/046* (2013.01); *A61B 5/0456* (2013.01); *A61B 5/1118* (2013.01)

(58) Field of Classification Search
CPC .. A61B 5/046; A61B 5/1118; A61B 5/0456; A61B 5/255; A61B 5/7257; A61B 5/02416; A61B 5/0432
See application file for complete search history.

(56) References Cited

U.S. PATENT DOCUMENTS

| 7,727,158 | B2 | 6/2010 | Kitajima et al. | |
| 7,738,936 | B1* | 6/2010 | Turcott | 600/339 |
| 2002/0028988 | A1 | 3/2002 | Suzuki et al. | |
| 2003/0130586 | A1* | 7/2003 | Starobin et al. | 600/515 |
| 2003/0181795 | A1 | 9/2003 | Suzuki et al. | |
| 2006/0161079 | A1 | 7/2006 | Choi et al. | |
| 2006/0224072 | A1 | 10/2006 | Shennib | |
| 2008/0249423 | A1 | 10/2008 | Kitajima et al. | |

(Continued)

FOREIGN PATENT DOCUMENTS

| JP | 1-221140 A | 9/1989 |
| JP | 2001-327472 A | 11/2001 |

(Continued)

OTHER PUBLICATIONS

Junichiro Hayano et al. *Spectral characteristics of ventricular response to atrial fibrillation*. Am J Physiol Heart Circ Physiol. 273:H2811-H2816.1997.

Non-Final Office Action dated Oct. 29, 2015 in related U.S. Appl. No. 14/197,050; 24 pages.

*Primary Examiner* — Rex R Holmes
(74) *Attorney, Agent, or Firm* — Kilpatrick Townsend & Stockton LLP

(57) ABSTRACT

An atrial fibrillation analyzer includes: an acquisition unit that acquires a detected waveform signal indicating a detection result of a pulse wave or an electrocardiogram; an RR interval calculation unit that calculates, on the basis of a spectrum of each unit period obtained by frequency analysis performed on the acquired detected waveform signal every unit period longer than 4 seconds and equal to or shorter than 16 seconds, a parameter corresponding to an average RR interval of the unit period every unit period; a power calculation unit that calculates power of a frequency band determined in advance in an RR waveform signal indicating a temporal change of the average RR interval calculated by the RR interval calculation unit; and an analysis unit that determines whether or not the power satisfies specific conditions and outputs information indicating presence of atrial fibrillation from the determination result.

13 Claims, 14 Drawing Sheets

(56) References Cited

U.S. PATENT DOCUMENTS

| | | |
|---|---|---|
| 2009/0076559 A1 | 3/2009 | Libbus et al. |
| 2009/0264783 A1* | 10/2009 | Xi et al. .................. 600/518 |
| 2010/0049266 A1 | 2/2010 | Ochs et al. |
| 2012/0095358 A1 | 4/2012 | Matsunaga et al. |
| 2012/0165684 A1 | 6/2012 | Sholder |
| 2013/0060154 A1* | 3/2013 | Morita ..................... 600/501 |
| 2014/0257123 A1* | 9/2014 | Watanabe ............ A61B 5/0456 600/518 |

FOREIGN PATENT DOCUMENTS

| | | |
|---|---|---|
| JP | 2006-061416 A | 3/2006 |
| JP | 2007-125366 A | 5/2007 |
| JP | 2008-253579 A | 10/2008 |
| JP | 2009-089883 A | 4/2009 |
| JP | 2013-055982 A | 4/2009 |
| JP | 3159276 U | 4/2010 |
| JP | 2012-081194 A | 4/2012 |

\* cited by examiner

ATRIAL FIBRILLATION ANALYZER AND PROGRAM

This application claims priority to Japanese Patent Application No. 2013-045572, filed Mar. 7, 2013, the entirety of which is hereby incorporated by reference.

BACKGROUND

1. Technical Field

The present invention relates to a technique of analyzing atrial fibrillation.

2. Related Art

In the medical field related to heart disease, there is a technique of determining atrial fibrillation. JP-A-2009-89883 discloses a technique of measuring the RR interval obtained from an electrocardiogram of each beat and determining atrial fibrillation on the basis of the standard deviation and the frequency distribution. Hayano J, Yamasaki F, Sakata S, Okada A, Mukai S, Fujinami T "Spectral characteristics of ventricular response to atrial fibrillation" Am. J. Physiol. 1997; 273: H2811-H2816 discloses that the RR interval during atrial fibrillation is irregular, a $1/f\beta$ component is present when the frequency analysis of cardiac beats of atrial fibrillation is performed, and a white noise pattern appears due to this variation.

In JP-A-2009-89883 and Hayano J, Yamasaki F, Sakata S, Okada A, Mukai S, Fujinami T "Spectral characteristics of ventricular response to atrial fibrillation" Am. J. Physiol. 1997; 273: H2811-H2816, it is necessary to measure the RR interval of each beat accurately for the exact determination of atrial fibrillation. The RR interval can be measured not only from the electrocardiogram waveform signal obtained by measuring an electrocardiogram but also from the pulse wave signal obtained by measuring a pulse wave.

However, in the case of measuring the pulse wave, the subject can move freely during the measurement in many cases. Accordingly, the influence of body movement noise is likely to be included in the pulse wave signal. Also in the case of measuring the electrocardiogram, the influence of body movement noise is likely to be included in the waveform signal of the electrocardiogram although there is a difference compared with the case where the pulse wave is measured. When there is such influence of body movement noise, it is very difficult to measure the RR interval of each beat accurately.

For this reason, when the measurement of exact RR interval of each beat is a precondition as in JP-A-2009-89883 and Hayano J, Yamasaki F, Sakata S, Okada A, Mukai S, Fujinami T "Spectral characteristics of ventricular response to atrial fibrillation" Am. J. Physiol. 1997; 273: H2811-H2816, it has not been possible to determine atrial fibrillation using a signal in which the influence of body movement noise is included.

SUMMARY

An advantage of some aspects of the invention is to analyze atrial fibrillation from a signal from which an RR interval can be measured, such as a pulse wave signal and a waveform signal of an electrocardiogram, even if influence of body movement noise is included in the signal.

An aspect of the invention is directed to an atrial fibrillation analyzer including: an acquisition unit that acquires a detected waveform signal indicating a detection result of a pulse wave or an electrocardiogram; an RR interval calculation unit that calculates, on the basis of a spectrum of each unit period obtained by frequency analysis performed on the acquired detected waveform signal every unit period longer than 4 seconds and equal to or shorter than 16 seconds, a parameter corresponding to an average RR interval of the unit period every unit period; a power calculation unit that calculates power of a frequency band determined in advance in an RR waveform signal indicating a temporal change of the average RR interval calculated by the RR interval calculation unit; and an analysis unit that determines whether or not the power satisfies specific conditions and outputs information indicating presence of atrial fibrillation from the determination result.

According to this atrial fibrillation analyzer, even if the influence of body movement noise is included in a signal, such as a pulse wave signal and a waveform signal of an electrocardiogram, from which an RR interval can be measured, it is possible to determine atrial fibrillation from the signal.

The atrial fibrillation analyzer described above may further include a variation coefficient calculation unit that calculates a variation coefficient of the average RR interval in the RR waveform signal, and the analysis unit may determine whether or not a set of the power and the variation coefficient satisfies the specific conditions and output information indicating presence of atrial fibrillation from the determination result.

The analysis unit may divide a plurality of sets of the power and the variation coefficients, which are obtained in a plurality of unit periods, into a first cluster of relatively high power and relatively high variation coefficients and a second cluster of relatively low power and relatively low variation coefficients, and determine the presence of atrial fibrillation using conditions, which are based on positional relationship between a first center of gravity of the first cluster and a second center of gravity of the second cluster in variation coefficient-power space, as the specific conditions.

According to this atrial fibrillation analyzer, it is possible to determine the presence of atrial fibrillation using the average RR interval.

The specific conditions may be conditions in which the first and second centers of gravity are separated from each other by a first threshold value, which is determined in advance, or more. When it is determined that the specific conditions are satisfied, the analysis unit may determine that the first cluster is in a state where atrial fibrillation has developed.

According to this atrial fibrillation analyzer, it is possible to determine the presence of atrial fibrillation using the clustering result.

The specific conditions may be conditions in which an average center of gravity of the first and second centers of gravity has power equal to or higher than a second threshold value determined in advance and a variation coefficient equal to or higher than a third threshold value determined in advance when the first and second centers of gravity are not separated from each other by the first threshold value or more. When it is determined that the specific conditions are satisfied, the analysis unit may determine that the first and second clusters are in a state where atrial fibrillation has developed.

The specific conditions may be conditions in which the average center of gravity of the first and second centers of gravity does not have at least one of power equal to or higher than the second threshold value and a variation coefficient equal to or higher than the third threshold value when the first and second centers of gravity are not separated from each other by the first threshold value or more. When it is determined that the specific conditions are satisfied, the analysis unit may determine that the first and second clusters are in a state where atrial fibrillation has not developed.

According to this atrial fibrillation analyzer, even if the first and second clusters are close to each other, it is possible to determine the presence of atrial fibrillation.

A minimum frequency of the frequency band may be equal to or greater than a reciprocal of the unit period.

According to this atrial fibrillation analyzer, it is possible to improve the accuracy of the determination of atrial fibrillation.

A maximum frequency of the frequency band may be equal to or less than ½ of a sampling frequency in the frequency analysis.

According to this atrial fibrillation analyzer, it is possible to improve the accuracy of the determination of atrial fibrillation.

The atrial fibrillation analyzer described above may further include: a detection unit that detects the pulse wave or the electrocardiogram of a target person; and a notification unit that notifies a user based on information output from the analysis unit. The acquisition unit may acquire a detected waveform signal obtained according to the detection result.

According to this atrial fibrillation analyzer, the target person can check the determination result of atrial fibrillation in real time.

The acquisition unit may include a noise reduction unit that performs a filtering process for reducing a body movement noise component on the detected waveform signal and outputs the result as the detected waveform signal.

According to this atrial fibrillation analyzer, it is possible for the target person to check the determination result of atrial fibrillation in real time while improving the accuracy of the determination of atrial fibrillation.

Another aspect of the invention is directed to a program causing a computer to execute: acquiring a detected waveform signal indicating a detection result of a pulse wave or an electrocardiogram; calculating, on the basis of a spectrum of each unit period obtained by frequency analysis performed on the acquired detected waveform signal every unit period longer than 4 seconds and equal to or shorter than 16 seconds, a parameter corresponding to an average RR interval of the unit period every unit period; calculating power of a frequency band determined in advance in an RR waveform signal indicating a temporal change of the calculated average RR interval; determining whether or not the power satisfies specific conditions; and outputting information indicating presence of atrial fibrillation from the determination result.

According to this program, even if the influence of body movement noise is included in a signal, such as a pulse wave signal and a waveform signal of an electrocardiogram, from which an RR interval can be measured, it is possible to determine atrial fibrillation from the signal.

BRIEF DESCRIPTION OF THE DRAWINGS

The invention will be described with reference to the accompanying drawings, wherein like numbers reference like elements.

DESCRIPTION OF EXEMPLARY EMBODIMENTS

Embodiments

Outline

When determining (analyzing) the atrial fibrillation from an electrocardiogram in the related art, an RR interval (hereinafter, referred to as an "electrocardiogram RR interval") of each beat has been used. In contrast, in the present embodiment, atrial fibrillation is determined from the pulse wave. When using the pulse wave, it may be difficult to specify the RR interval of each beat accurately unlike the electrocardiogram. For this reason, in the present embodiment, a value indicating the average of the RR interval (hereinafter, referred to as an "average pulse wave RR interval") within a certain unit time (frame) is used. Here, an atrial fibrillation determination method using the electrocardiogram RR interval will be described first, and then problems when using the average pulse wave RR interval will be described. Finally, the outline of the determination method according to the present embodiment will be described.

Figure 9A:
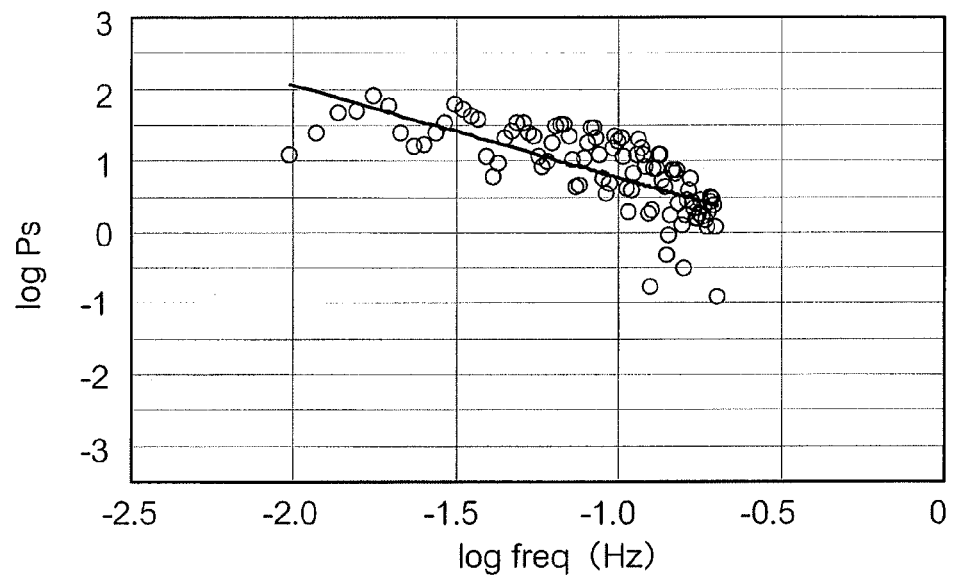
FIGS. 9A and 9B are diagrams illustrating an atrial fibrillation analysis method using the electrocardiogram RR interval.
Figure 9B:
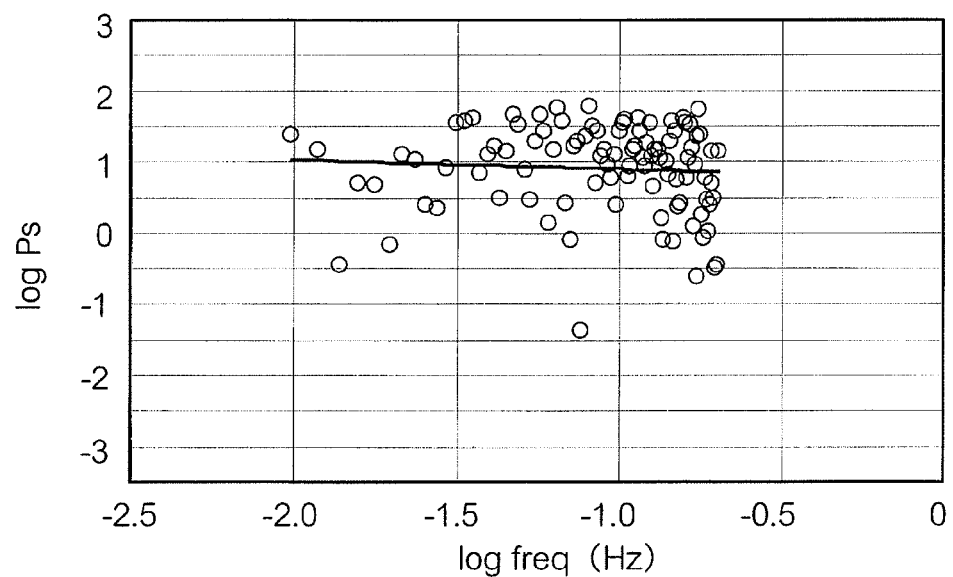

FIGS. 9A and 9B are diagrams illustrating an atrial fibrillation analysis method using the electrocardiogram RR interval. FIGS. 9A and 9B are graphs expressed by performing frequency analysis in a band of 0.01 Hz to 0.2 Hz of one frame (480 seconds) for a waveform signal indicating a change in the electrocardiogram RR interval and performing logarithmic conversion of a peak frequency and power. FIG. 9A shows a case of using the electrocardiogram RR interval when atrial fibrillation has not developed, and FIG. 9B shows a case of using the electrocardiogram RR interval when atrial fibrillation has developed. The straight line in the diagram shows a linear regression line obtained from the plotted data. The result when the correlation coefficient γ and the inclination β of the linear regression line are calculated from these graphs is as follows.

In the case where atrial fibrillation has not developed as shown in FIG. 9A, γ=−0.72 and β=−1.29. In addition, in the case where atrial fibrillation has developed as shown in FIG. 9B, γ=−0.07 and β=−0.13. Thus, when atrial fibrillation has developed, it can be seen that correlation is lost and a white noise pattern appears and that the inclination β is close to "0". Accordingly, when using the electrocardiogram RR interval, the presence of atrial fibrillation can be determined from the correlation coefficient γ and the inclination β of the linear regression line in a plot of peak frequency and power.

Figure 10A:
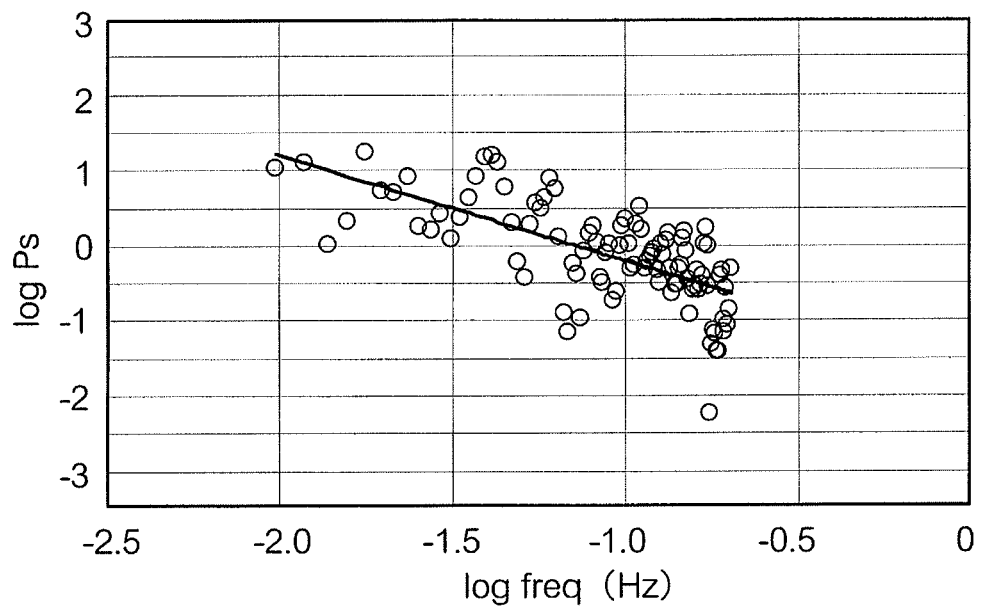
FIGS. 10A and 10B are diagrams illustrating the problems of the atrial fibrillation analysis method using the average pulse wave RR interval.
Figure 10B:
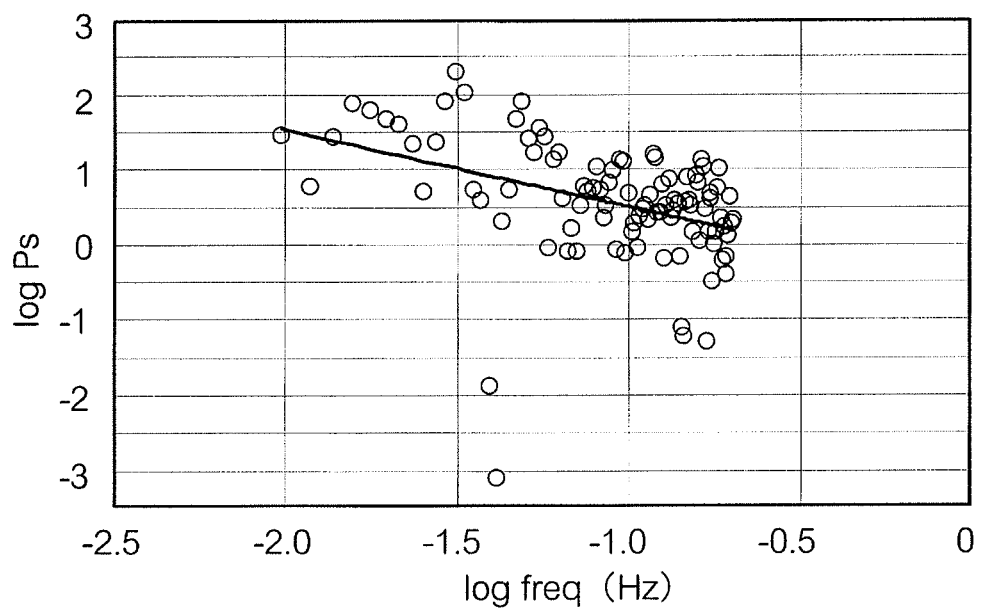

FIGS. 10A and 10B are diagrams illustrating the problems of the atrial fibrillation analysis method using the average pulse wave RR interval. FIGS. 10A and 10B are graphs expressed by performing frequency analysis in a band of 0.01 Hz to 0.2 Hz of one frame (480 seconds) for a waveform signal indicating a change in the average pulse wave RR interval and performing logarithmic conversion of a peak frequency and power. FIG. 10A shows an example where atrial fibrillation has not developed, and FIG. 10B shows an example where atrial fibrillation has developed. The straight line in the diagram shows a linear regression line obtained from the plotted data.

In the case where atrial fibrillation has not developed as shown in FIG. 10A, γ=−0.68 and β=−1.40. In addition, in the case where atrial fibrillation has developed as shown in FIG. 10B, γ=−0.41 and β=−1.02. Thus, when using the average pulse wave RR interval, there is no significant difference of γ and β due to the presence of atrial fibrillation, as shown in FIGS. 10A and 10B. Accordingly, determination of the presence of atrial fibrillation is difficult if the same method as when using the electrocardiogram RR interval is used.

Here, if FIGS. 9A and 9B are compared again, it can be seen that the power is increased on the high frequency band side when atrial fibrillation has developed. For example, in FIGS. 9A and 9B, when comparing the power for a frequency band around 0.2 Hz, power when atrial fibrillation has not developed is "1.59" and power when atrial fibrillation has developed is "4.97". When atrial fibrillation has developed, the power in this frequency band is increased several times and accordingly a significant difference can be seen, compared with when atrial fibrillation has not developed.

This increase in power is also observed when using the average pulse wave RR interval. In FIGS. 10A and 10B, when comparing the power for a frequency band around 0.2 Hz, power when atrial fibrillation has not developed is "0.05" and power when atrial fibrillation has developed is "0.30". Thus, even if the average pulse wave RR interval is used, when atrial fibrillation has developed, the power in this frequency band is increased several times and accordingly a significant difference can be seen, compared with when atrial fibrillation has not developed. In the present embodiment, the presence of atrial fibrillation is determined using the increase in power as an indicator.

In the present embodiment, a variation coefficient is used as another indicator of the presence of atrial fibrillation. The variation coefficient is a parameter indicating the degree of a variation with respect to the average of the average pulse wave RR interval. When atrial fibrillation develops, irregularity of the RR interval occurs. That is, the time interval of each beat becomes irregular. The same is true for the average pulse wave RR interval, and an irregular state (average variation) can be an indicator of atrial fibrillation. In the present embodiment, the presence of atrial fibrillation is determined using the power and the variation coefficient as indicators. Hereinafter, the device configuration and operation in the present embodiment will be described in detail.

Configuration of a Pulse Wave Measuring Device 1

Figure 1A:
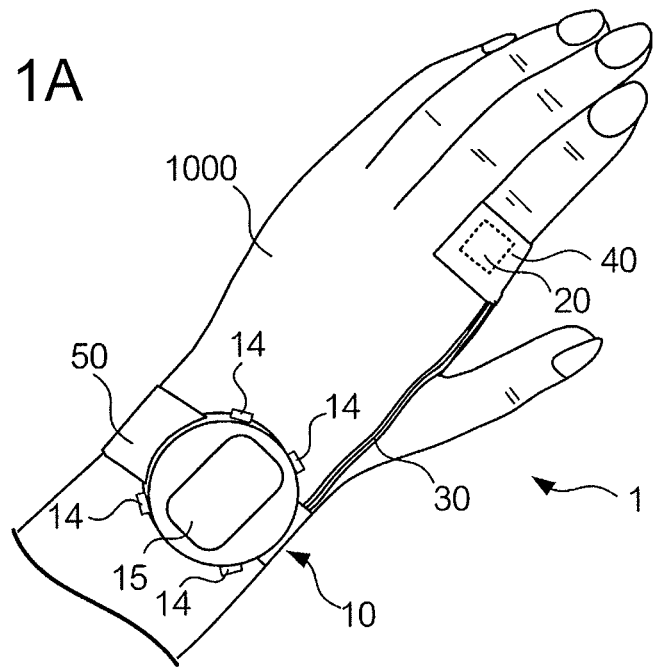
FIGS. 1A and 1B are diagrams illustrating the appearance of a pulse wave measuring device according to an embodiment.
Figure 1B:
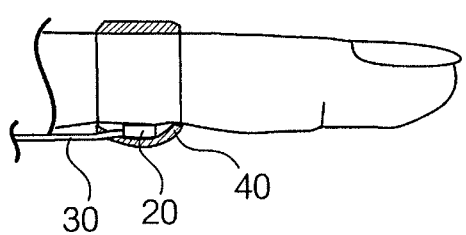

FIGS. 1A and 1B are diagrams illustrating the appearance of a pulse wave measuring device 1 according to the embodiment. As shown in FIG. 1A, the pulse wave measuring device 1 according to the embodiment of the invention includes a device body 10 mounted in the manner of a wristwatch on a wrist portion (arm) in a hand 1000 of a target person, who is a user, and a pulse wave detector 20 that is mounted on a detection portion and detects a pulse wave. The device body 10 and the pulse wave detector 20 are connected to each other through a cable 30. Through the cable 30, a pulse wave signal (hereinafter, referred to as a detected waveform signal L) output from the pulse wave detector 20 is supplied to the device body 10 and electric power from the device body 10 is supplied to the pulse wave detector 20.

A wristband 50 is attached to the device body 10. The device body 10 is mounted on the arm by wrapping the wristband 50 around the arm of the user. An operation unit 14 and a display unit 15 are provided in the device body 10. The operation unit 14 is an operator such as a button switch used when the user inputs an instruction for function selection or the like to the pulse wave measuring device 1. A touch sensor or the like provided on the display unit 15 may be included in the operation unit 14. The display unit 15 is a display device, such as a liquid crystal display or an organic EL display.

As shown in FIG. 1B, in this example, a detection portion on which the pulse wave detector 20 is mounted is assumed to be a part of a region from the base of the index finger to the second finger joint in the hand 1000. However, the detection portion on which the pulse wave detector 20 is mounted may be any portion as long as it is a portion in which a pulse wave can be detected. The pulse wave detector 20 is mounted on the detection portion by being fixed by a fixing band 40. In this case, the fixing band 40 is in a state covering the pulse wave detector 20, and a light receiving unit of the pulse wave detector 20 is shielded so that light from the outside of the fixing band 40 does not reach the light receiving unit.

The pulse wave detector 20 detects a pulse wave as follows, and outputs the detected waveform signal L indicating the detection result. The pulse wave detector 20 includes a light emitting unit (for example, a green light emitting diode (LED)) and a light receiving unit. The pulse wave detector 20 emits light corresponding to the electric power, which is supplied from the device body 10 through the cable 30, from the light emitting unit. The pulse wave detector 20 receives light reflected by hemoglobin in the capillaries, of the light from the light emitting unit, through the light receiving unit, and supplies a signal corresponding to the light receiving level to the device body 10 through the cable 30 as the detected waveform signal L.

Figure 2:
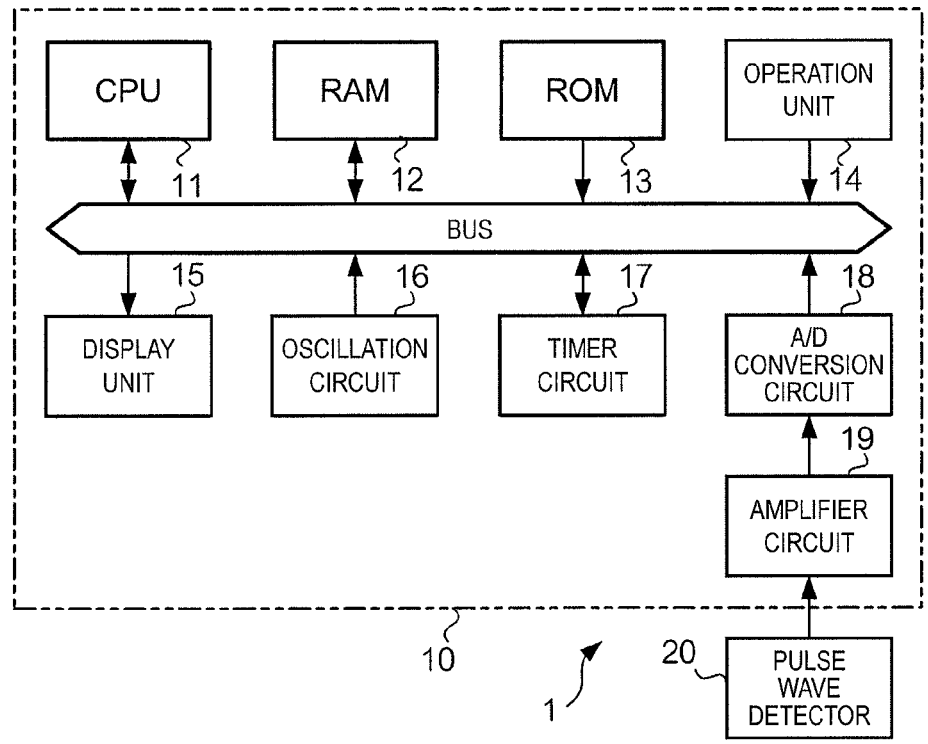
FIG. 2 is a diagram illustrating the configuration of the pulse wave measuring device according to the embodiment.

FIG. 2 is a diagram illustrating the configuration of the pulse wave measuring device 1 according to the embodiment. The pulse wave measuring device 1 includes: the device body 10 including a central processing unit (CPU) 11, a random access memory (RAM) 12, a read only memory (ROM) 13, the operation unit 14, the display unit 15, an oscillation circuit 16, a timer circuit 17, an A/D conversion circuit 18, and an amplifier circuit 19; and the pulse wave detector 20. The respective components excluding the amplifier circuit 19 and the pulse wave detector 20 are connected to each other through a bus.

The CPU 11 performs control of each component, data transmission, and the like according to a control program stored in the ROM 13. The RAM 12 temporarily stores biological information, such as the detected waveform signal L, and various kinds of data generated during the execution of the control program in the CPU 11. The CPU 11 realizes an atrial fibrillation analysis function by executing the control program, so that the pulse wave measuring device 1 functions as an atrial fibrillation analyzer. In addition, the CPU 11 may realize various functions other than the atrial fibrillation determination function by executing the control program. It is preferable to realize these functions, for example, by causing the user to operate the operation unit 14.

As described above, the operation unit 14 includes button switches for inputting an instruction of the user to the pulse wave measuring device 1. When the operation unit 14 is operated by the user, the operation unit 14 outputs an operation signal indicating the operation content to the CPU 11.

The display unit 15 includes a display device, such as a liquid crystal display or an organic EL display, as described above, and the display content is controlled by the CPU 11. This display content is various images indicating time display, various menu screens, a pulse wave measurement result, and an atrial fibrillation determination result, for example.

The oscillation circuit 16 supplies a clock signal as a basis for control to the CPU 11.

The timer circuit 17 measures the time under the control of the CPU 11.

The amplifier circuit 19 amplifies the detected waveform signal L supplied from the pulse wave detector 20 through the cable 30. The gain at the time of amplification is set by the control of the CPU 11.

The A/D conversion circuit 18 converts the detected waveform signal L, which is an analog signal, amplified by the amplifier circuit 19 into a digital signal. In this example, the sampling frequency is 100 Hz, and is a sufficiently high frequency compared with an RR interval obtained from the pulse wave. In addition, in this example, quantization is performed in 10 bits. In addition, for the sampling frequency and the quantization bit, different values may be determined according to the required accuracy.

Subsequently, the functional configuration (atrial fibrillation analysis function) of the atrial fibrillation analyzer realized by the CPU 11 will be described.

Functional Configuration

Figure 3:
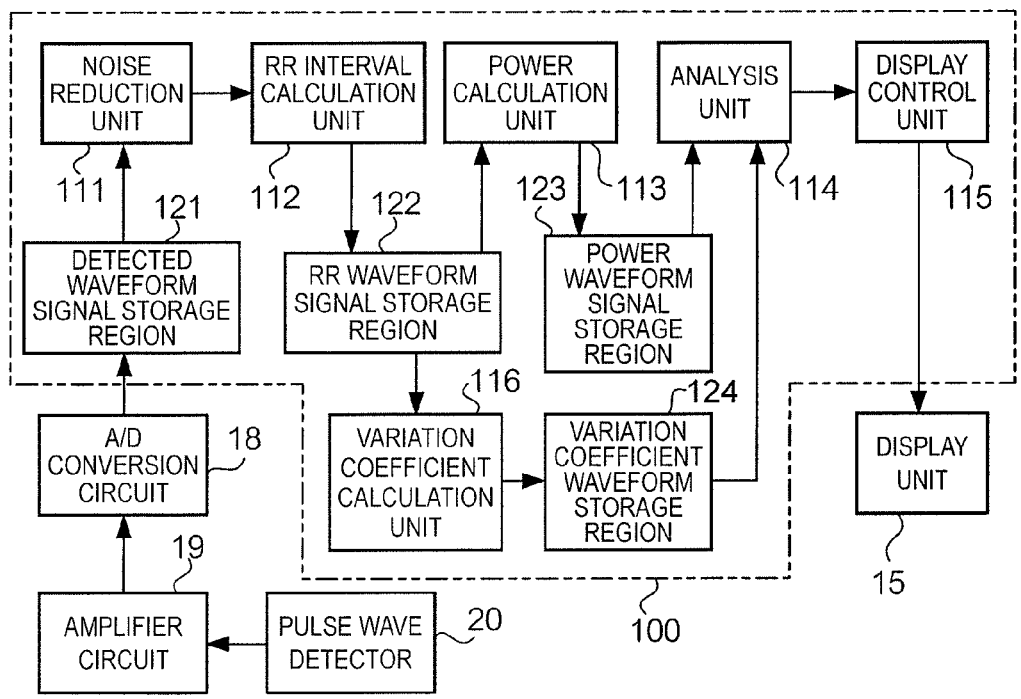
FIG. 3 is a diagram illustrating the functional configuration of an atrial fibrillation analyzer according to the embodiment.

FIG. 3 is a diagram illustrating the functional configuration of an atrial fibrillation analyzer 100 according to the embodiment. The atrial fibrillation analyzer 100 includes a noise reduction unit 111, an RR interval calculation unit 112, a power calculation unit 113, a determination unit 114, a display control unit 115, and a variation coefficient calculation unit 116, and is realized by each functional configuration of a detected waveform signal storage region 121, an RR waveform signal storage region 122, a power waveform signal storage region 123, a variation coefficient waveform storage region 124 that are storage regions of various kinds of data.

The detected waveform signal storage region 121 is a region provided on the RAM 12 in which the detected waveform signal L converted into a digital signal by the A/D conversion circuit 18 is stored.

The noise reduction unit 111 performs a filtering process for reducing body movement noise components other than the frequency band, which corresponds to the RR interval, from the detected waveform signal L stored in the detected waveform signal storage region 121 and outputs the result. Examples of the filtering process include a process of a high pass filter, a process of a band pass filter, and a process of an adaptive filter. The detected waveform signal L from which body movement noise components have been reduced by the noise reduction unit 111 may be temporarily stored in the RAM 12. The noise reduction unit 111 and the detected waveform signal storage region 121 function as an acquisition unit that acquires the detected waveform signal L used in the frequency analysis of the RR interval calculation unit 112.

In addition, since the body movement noise components are reduced by this filtering process, the influence is reduced from the detected waveform signal L. However, it is not possible to measure the exact RR interval so as to be able to determine atrial fibrillation accurately in the technique (JP-A-2009-89883 and Hayano J, Yamasaki F, Sakata S, Okada A, Mukai S, Fujinami T "Spectral characteristics of ventricular response to atrial fibrillation" Am. J. Physiol. 1997; 273: H2811-H2816) presented as the related art.

For the detected waveform signal L from which body movement noise components have been reduced by the noise reduction unit 111, the RR interval calculation unit 112 cuts a frame in each sampling, and calculates a frequency spectrum by frequency analysis in a short time (STFT (Short-Time Fourier Transform) analysis). Then, the RR interval calculation unit 112 calculates a parameter corresponding to the RR interval for each frame on the basis of the calculated frequency spectrum, and stores an RR waveform signal FRR, which indicates a temporal change of the parameter, in the RR waveform signal storage region 122 provided on the RAM 12. In addition, the RR waveform signal FRR is a set of data indicating a temporal change of this parameter.

In this example, the calculated parameter is a value (average pulse wave RR interval) indicating the average of the RR interval in a frame. For example, the calculated parameter is a frequency at which a maximum peak of the frequency spectrum is obtained. Accordingly, the RR waveform signal FRR indicates a temporal change of the average pulse wave RR interval. By the process of the RR interval calculation unit 112, the influence of the body movement noise included in the RR waveform signal FRR can be greatly reduced even if the body movement noise is not completely removed by the noise reduction unit 111.

Figure 4:
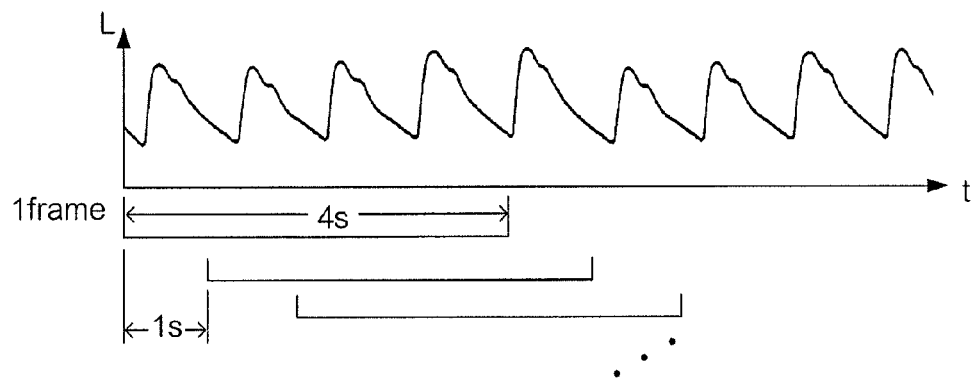
FIG. 4 is a diagram illustrating a frame when performing frequency analysis of a detected waveform signal.

FIG. 4 is a diagram illustrating a frame when performing frequency analysis of the detected waveform signal L. The waveform shown in FIG. 4 is an example of the waveform of the detected waveform signal L. As shown in FIG. 4, the period of each frame is 4 seconds in this example, and frequency analysis is performed after sampling every 1 second. That is, each frame is set so as to be shifted by 1 second, and overlaps the next frame for 3 seconds. Since the sampling timing and a frame are set as described above, the average pulse wave RR interval is an average value of 4 seconds of the RR interval, and the RR waveform signal FRR indicates a change in the average pulse wave RR interval every second.

Figure 5:
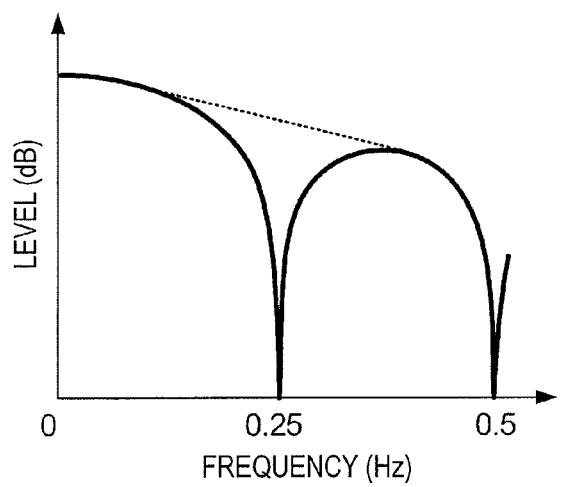
FIG. 5 is a diagram illustrating the frequency characteristics in an RR interval calculation unit.

FIG. 5 is a diagram illustrating the frequency characteristics in the RR interval calculation unit 112. Performing frequency analysis with the frame set as described above in the RR interval calculation unit 112 is equivalent to "frequency characteristics are superimposed in the movement averaging process". In the frequency characteristics shown in FIG. 5, valleys occur at the frequency of 0.25 Hz equivalent to 4 seconds of the time of the frame and frequencies of integral multiples of 0.25 Hz. In addition, as an overall trend when connecting the peaks of the mountains, the level becomes lower as the frequency becomes higher. That is, the frequency characteristics shown in FIG. 5 are frequency characteristics having a negative inclination. The inclination becomes steeper as the period of a frame becomes longer. On the other hand, as the period of a frame becomes shorter, the inclination becomes close to "0", but the amount of body movement noise components in the detected waveform signal L is increased. Therefore, it is preferable to set the frame period to 1 second or more and 16 seconds or less, it is more preferable to set the frame period to be longer than 4 seconds and equal to or shorter than 16 seconds or less, and it is most preferable to set the frame period to be longer than 4 seconds and equal to or shorter than 8 seconds.

This point will be described in more detail. When atrial fibrillation occurs, a variation occurs in the RR interval (equivalent to the peak interval of a pulse wave signal). When the RR interval of each beat is taken as a time series change, an abrupt change in the RR interval can be seen at the time of occurrence of atrial fibrillation. In this case, a frequency component of the RR interval variation due to atrial fibrillation appears in a band of 0.2 Hz to 1.0 Hz.

Figure 16:
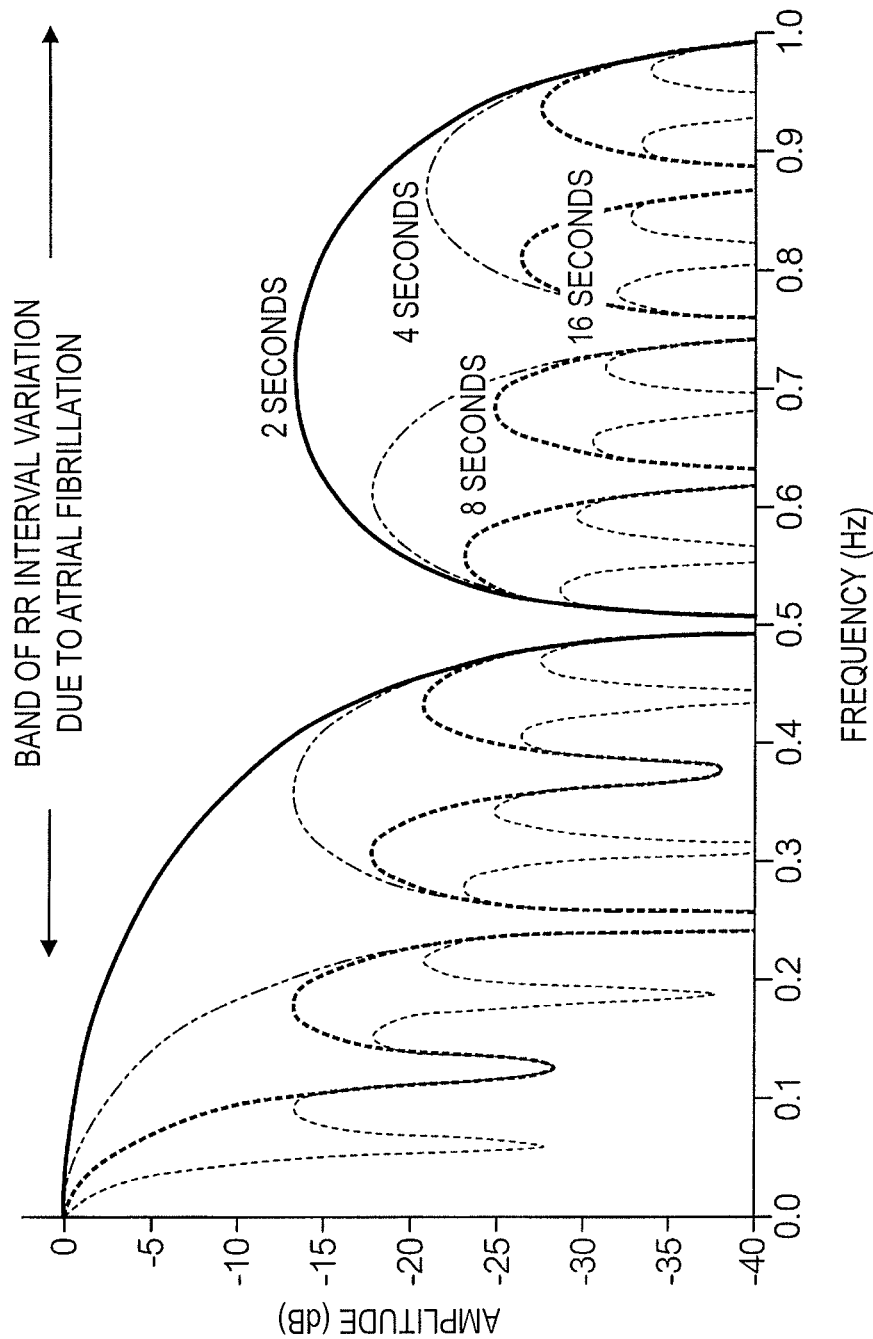
FIG. 16 is a diagram illustrating the frequency characteristics of the RR interval.

FIG. 16 is a diagram illustrating the frequency characteristics of the RR interval. Performing frequency analysis with the frame of a determined length as a unit is the same as "frequency characteristics are superimposed in the movement averaging process". FIG. 16 shows a frequency-amplitude characteristics when changing the time length of the frame. The amplitude corresponding to the band of RR interval variation due to atrial fibrillation becomes lower as the frame period becomes longer. That is, it can be seen that it becomes relatively difficult to catch the RR interval variation due to atrial fibrillation as the frame period increases.

Figure 17:
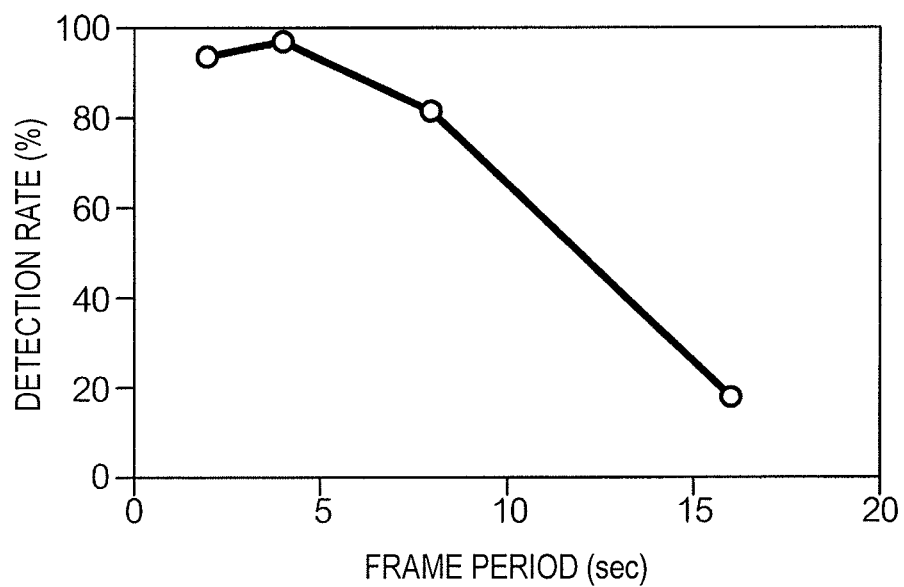
FIG. 17 is a diagram illustrating the detection rate of arrhythmia.

FIG. 17 is a diagram illustrating the detection rate of arrhythmia. FIG. 17 shows a result of attempts to detect arrhythmia in a subject, who has arrhythmia including atrial fibrillation as a chronic disease, by changing the time length of the frame to various values in the method according to the present embodiment. In FIG. 17, the horizontal axis indicates the time length of the frame, and the vertical axis indicates the detection rate of arrhythmia. In the pulse wave data of the subject, the integral value of the power of the RR interval variation band shown in FIG. 16 has been calculated. When the variation power equal to or greater than a threshold is obtained, it has been determined that arrhythmia can be detected. As described above, it can be seen that it is not possible to catch the variation in the RR interval when the frame period is increased and accordingly, the detection rate becomes poor.

The power calculation unit 113 performs frequency analysis in a short time (STFT analysis) for the RR waveform signal FRR stored in the RR waveform signal storage region 122, and calculates power (hereinafter, referred to as band power) of a part of a frequency band (hereinafter, referred to as a calculation frequency band) on the basis of the obtained frequency spectrum. The power calculation unit 113 stores a power waveform signal Pa, which indicates a temporal change of the calculated band power, in the power waveform signal storage region 123 provided on the RAM 12. In addition, the power waveform signal Pa is a set of data indicating a temporal change of band power.

Figure 6:
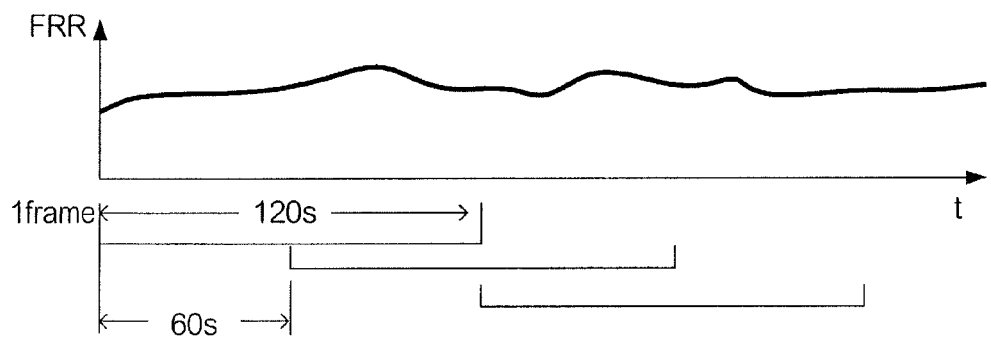
FIG. 6 is a diagram illustrating a frame when performing frequency analysis of an RR waveform signal.

FIG. 6 is a diagram illustrating a frame when performing frequency analysis of the RR waveform signal FRR. The waveform shown in FIG. 6 is an example of the waveform of the RR waveform signal FRR. As shown in FIG. 6, the period of each frame is 120 seconds in this example, and frequency analysis is performed after sampling every 60 seconds. That is, each frame is set so as to be shifted by 60 seconds, and overlaps the next frame for 60 seconds.

In addition, the above-described calculation frequency band from which band power is calculated by the power calculation unit 113 is determined in advance. In this example, the above-described calculation frequency band is assumed to be a band of 0.25 Hz to 0.5 Hz. This is determined as between two valleys (valleys of 0.25 Hz and 0.5 Hz) of the frequency characteristics shown in FIG. 5. The reason is that power in a valley portion hardly contributes to the determination of the presence of atrial fibrillation since the power in a valley portion is suppressed. For this reason, the calculation frequency band is determined to focus on a portion that contributes to the determination of the presence of atrial fibrillation. That is, the calculation frequency band may be set to be a narrow range in such a manner that a valley portion in the frequency characteristics is removed and only a mountain portion is included. For example, the calculation frequency band may be a band of 0.3 Hz to 0.45 Hz.

In addition, in this example, the maximum frequency (upper limit) and the minimum frequency (lower limit) of the calculation frequency band are determined according to the frequency characteristics in the RR interval calculation unit 112, that is, the period of a frame used in the frequency analysis of the RR interval calculation unit 112. On the other hand, one or both of the upper and lower frequencies do not necessarily need to be determined according to the period of a frame.

As shown in FIGS. 9A, 9B, 10A, and 10B, the minimum frequency of the calculation frequency band may be set to be equal to or higher than 0.1 Hz at which a change in power becomes apparent. Preferably, the minimum frequency of the calculation frequency band may be set to be equal to or higher than 0.2 Hz. In this case, as described above, it is preferable that the minimum frequency be equal to or greater than the reciprocal of the period of the frame used in the frequency analysis of the RR interval calculation unit 112.

In addition, it is preferable that the maximum frequency of the calculation frequency band be equal to or less than ½ of the sampling frequency in frequency analysis of the RR interval calculation unit 112 in consideration of the influence of the Nyquist frequency. In this case, as described above, it is preferable that the maximum frequency be equal to or less than twice the reciprocal of the period of the frame used in the frequency analysis of the RR interval calculation unit 112.

Referring back to FIG. 3, explanation is continued. The variation coefficient calculation unit 116 calculates a variation coefficient CVRR from the RR waveform signal FRR (average pulse wave RR interval), which is stored in the RR waveform signal storage region 122, according to the following Expression (1).

$$CVRR = \sigma RR / aveRR \quad (1)$$

In addition, $\sigma RR$ and $aveRR$ indicate a standard deviation and an average value of the average pulse wave RR interval in the period of one frame, respectively. That is, the variation coefficient CVRR is a parameter indicating the degree of a variation with respect to an average. The variation coefficient calculation unit 116 stores the calculated variation coefficient CVRR in the variation coefficient waveform storage region 124. Since the variation coefficient CVRR is calculated for each frame, a signal (hereinafter, referred to as a "variation coefficient signal Sc") indicating a temporal change of the variation coefficient CVRR is stored in the variation coefficient waveform storage region 124. In addition, the variation coefficient signal Sc is a set of data indicating a temporal change of the variation coefficient CVRR.

The determination unit 114 determines whether or not specific determination conditions are satisfied on the basis of the power waveform signal Pa stored in the power waveform signal storage region 123 and the variation coefficient signal Sc stored in the variation coefficient waveform storage region 124, and outputs information according to the determination result. The specific determination conditions will be described later.

When it is determined that there is atrial fibrillation, the determination unit 114 outputs information indicating the determination result to the display control unit 115. The information output from the determination unit 114 may be information regarding the presence of atrial fibrillation, for example, information indicating the determination as atrial fibrillation. The display control unit 115 controls the display content of the display unit 15 on the basis of the information output from the determination unit 114, and displays an image showing that determination as atrial fibrillation has been made. The user can check whether or not determination as atrial fibrillation has been made by viewing this display content. In addition, this display content may be a display showing a determination result of atrial fibrillation in real time, or may be a display showing a period determined to be atrial fibrillation.

The above is an explanation of the functional configuration of the atrial fibrillation analyzer 100. Subsequently, the operation (atrial fibrillation determination process) of the atrial fibrillation analyzer 100 will be described with reference to FIG. 8.

Atrial Fibrillation Determination Process

Figure 8:
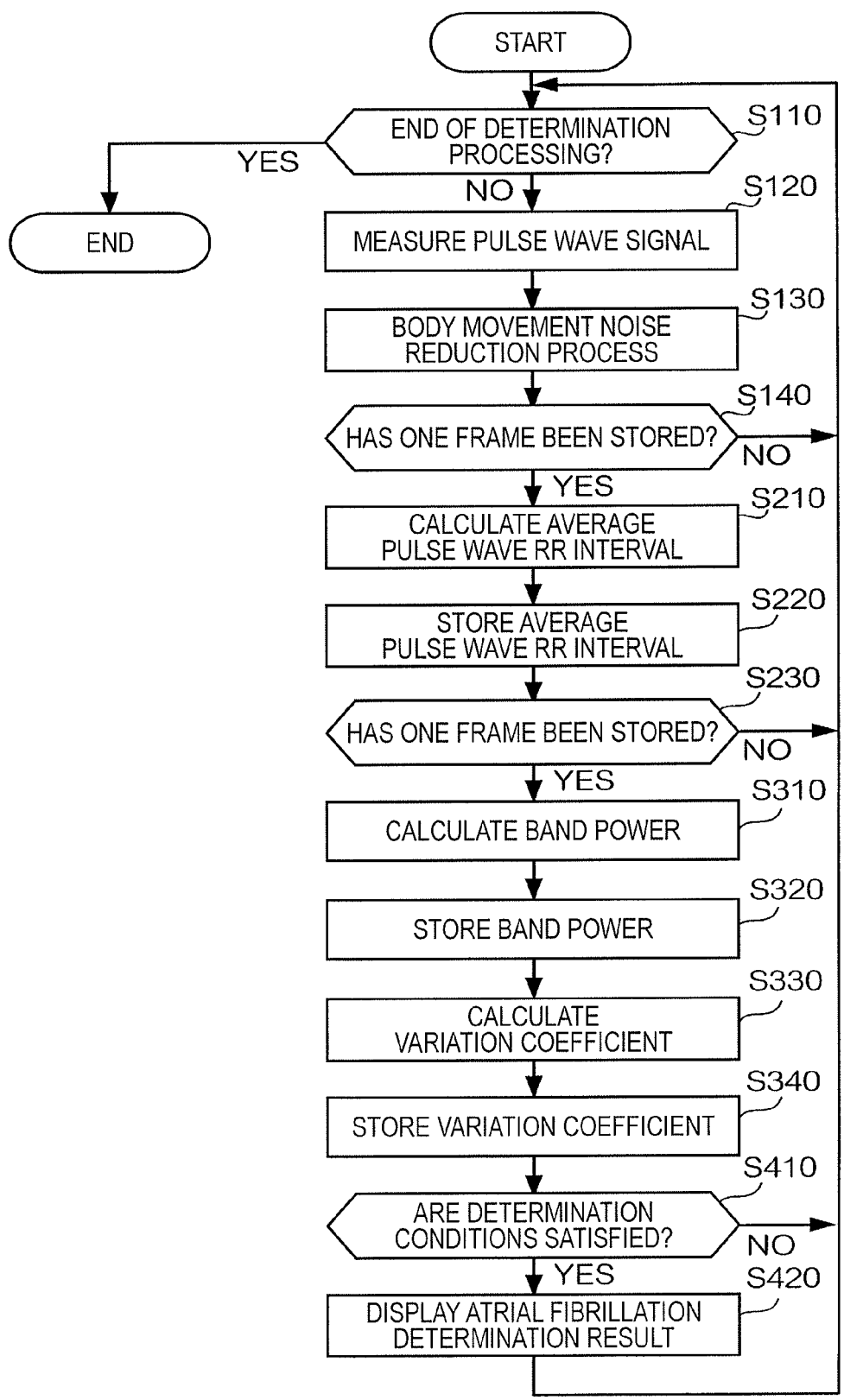
FIG. 8 is a flowchart of an atrial fibrillation analysis process.

FIG. 8 is a flowchart illustrating an atrial fibrillation determination process in the embodiment. First, when a user operates the operation unit 14 to input an instruction to start the atrial fibrillation determination process, the CPU 11 starts the flow shown in FIG. 8. The CPU 11 determines whether or not the user has operated the operation unit 14 to input an instruction to end the determination process (step S110). When an instruction to end the determination process is input (step S110; YES), the CPU 11 ends the atrial fibrillation determination process.

When an instruction to end the determination process is not input (step S110; NO), the CPU 11 measures the detected waveform signal L by detecting a pulse wave using the pulse wave detector 20 (step S120), and performs a body movement noise reduction process using the noise reduction unit 111 (step S130). In this case, the CPU 11 stores the detected waveform signal L in the detected waveform signal storage region 121 of the RAM 12. However, the detected waveform signal L after the body movement noise reduction process may be stored.

The CPU 11 determines whether or not the waveform signal after the body movement noise reduction process is stored by one frame in the RAM 12 (step S140). When one frame is not stored (step S140; NO), the CPU 110 returns to step S110 to continue the process. On the other hand, when one frame is stored (step S140; YES), the CPU 11 calculates an average pulse wave RR interval using the RR interval calculation unit 112 (step S210).

The CPU 11 stores the average pulse wave RR interval calculated by the RR interval calculation unit 112 in the RR waveform signal storage region 122 (step S220). A temporal change of the average pulse wave RR interval stored in the storage region is the RR waveform signal FRR.

The CPU 11 determines whether or not the RR waveform signal FRR stored in the RR waveform signal storage region 122 is stored by one frame (step S230). When one frame is not stored (step S230; NO), the CPU 110 returns to step S110 to continue the process. On the other hand, when one frame is stored (step S230; YES), the CPU 11 calculates band power using the power calculation unit 113 (step S310).

The CPU 11 stores the band power calculated by the power calculation unit 113 in the power waveform signal storage region 123 (step S320). A temporal change of the band power stored in the storage region is the power waveform signal Pa.

The CPU 11 calculates a variation coefficient using the variation coefficient calculation unit 116 (step S330). The CPU 11 stores the variation coefficient calculated by the variation coefficient calculation unit 116 in the variation coefficient waveform storage region 124 (step S340).

The CPU 11 causes the determination unit 114 to determine whether or not the power waveform signal Pa and the variation coefficient signal Sc satisfy predetermined determination conditions with reference to the power waveform signal Pa and the variation coefficient signal Sc that are stored (step S410).

Figure 11:
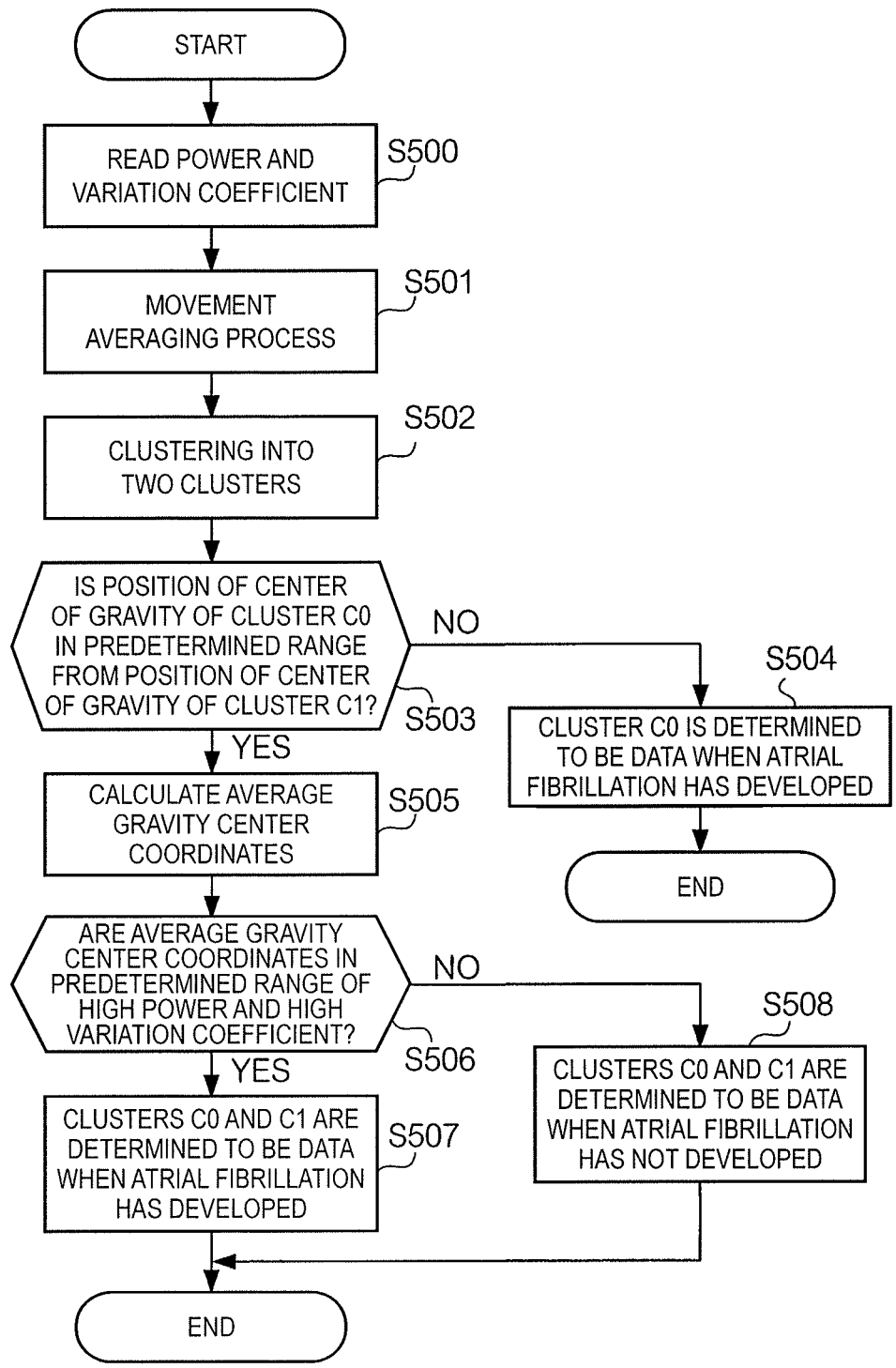
FIG. 11 is a diagram showing the details of the atrial fibrillation analysis process in step S410 of FIG. 8.

FIG. 11 is a diagram showing the details of the atrial fibrillation determination process in step S410. In step S500, the CPU 11 reads the power waveform signal Pa and the variation coefficient signal Sc from the RAM 12.

Figure 12:
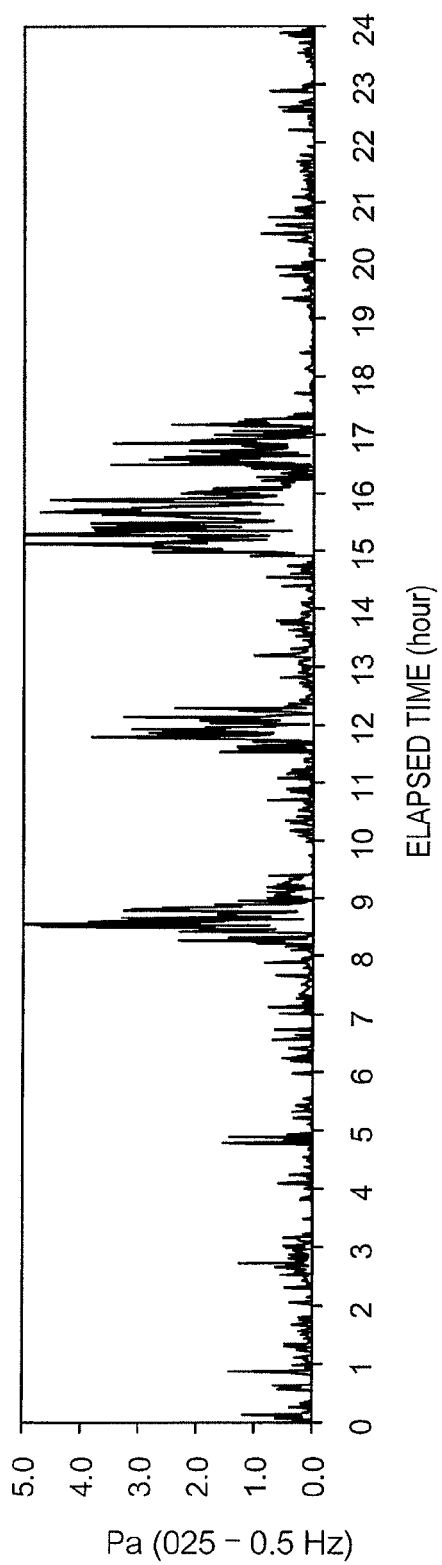
FIG. 12 is a diagram illustrating a power waveform signal and a variation coefficient signal.
Figure 12:
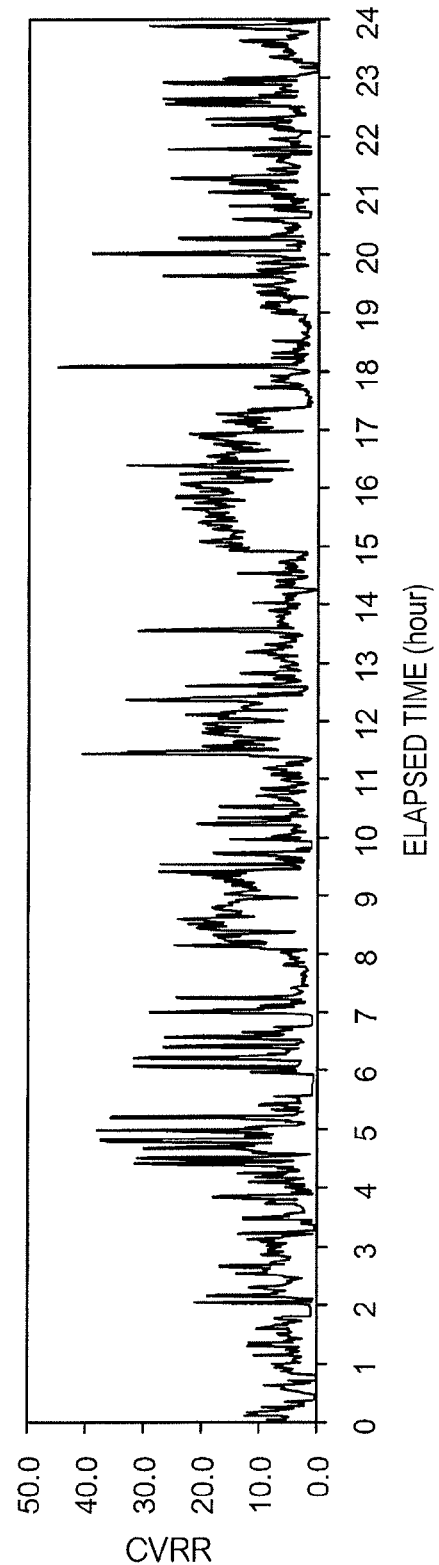

FIG. 12 is a diagram illustrating the power waveform signal Pa and the variation coefficient signal Sc. FIG. 12 shows the power waveform signal Pa [$msec^2$] and the variation coefficient signal Sc [%] obtained from a pulse wave signal measured for 24 hours for a certain patient. In addition, this patient has developed atrial fibrillation during the measurement period.

FIG. 11 is referred to again. In step S501, the CPU 11 performs a movement averaging process on the power waveform signal Pa and the variation coefficient signal Sc. The movement averaging process is performed in order to smooth small variations (variations in a short time) for each of the power and the variation coefficient CVRR. In this example, the movement averaging process is performed using the data (that is, data obtained from the 20-minute measurement of the pulse wave) of 20 points.

Figure 13:
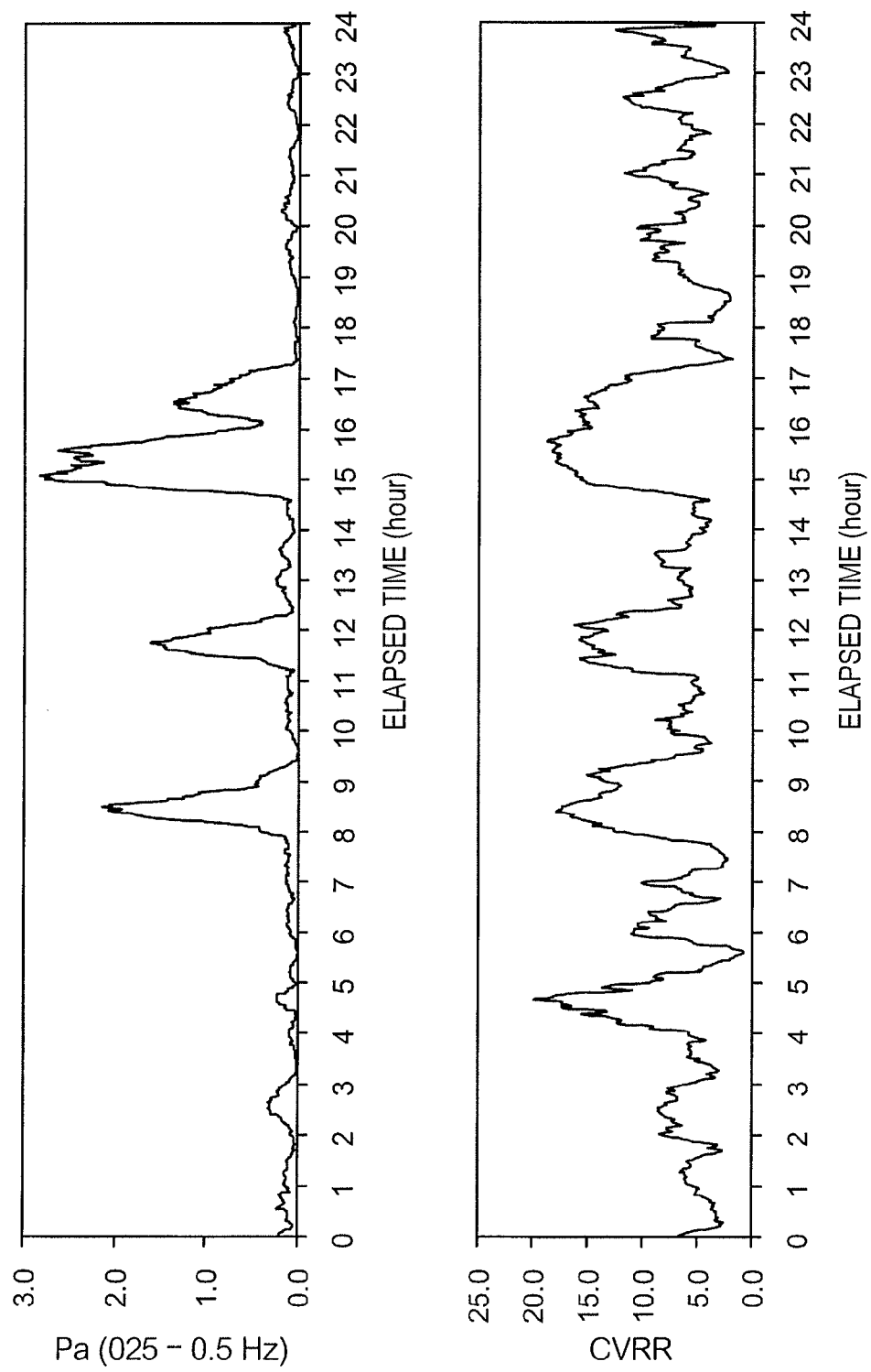
FIG. 13 is a diagram illustrating power and a variation coefficient after a movement averaging process.

FIG. 13 is a diagram illustrating the power waveform signal Pa and the variation coefficient signal Sc after the movement averaging process. Small variations are smoothed by the movement averaging process. Hereinafter, the data after the movement averaging process is treated as data showing the power and the variation coefficient at a certain time. Since the measurement is performed every 60 seconds, the data of 1440 points is obtained in the measurement of 24 hours.

FIG. 11 is referred to again. In step S502, the CPU 11 clusters the data into two clusters using a predetermined algorithm (for example, a k-means method widely known as a method of clustering).

Figure 14:
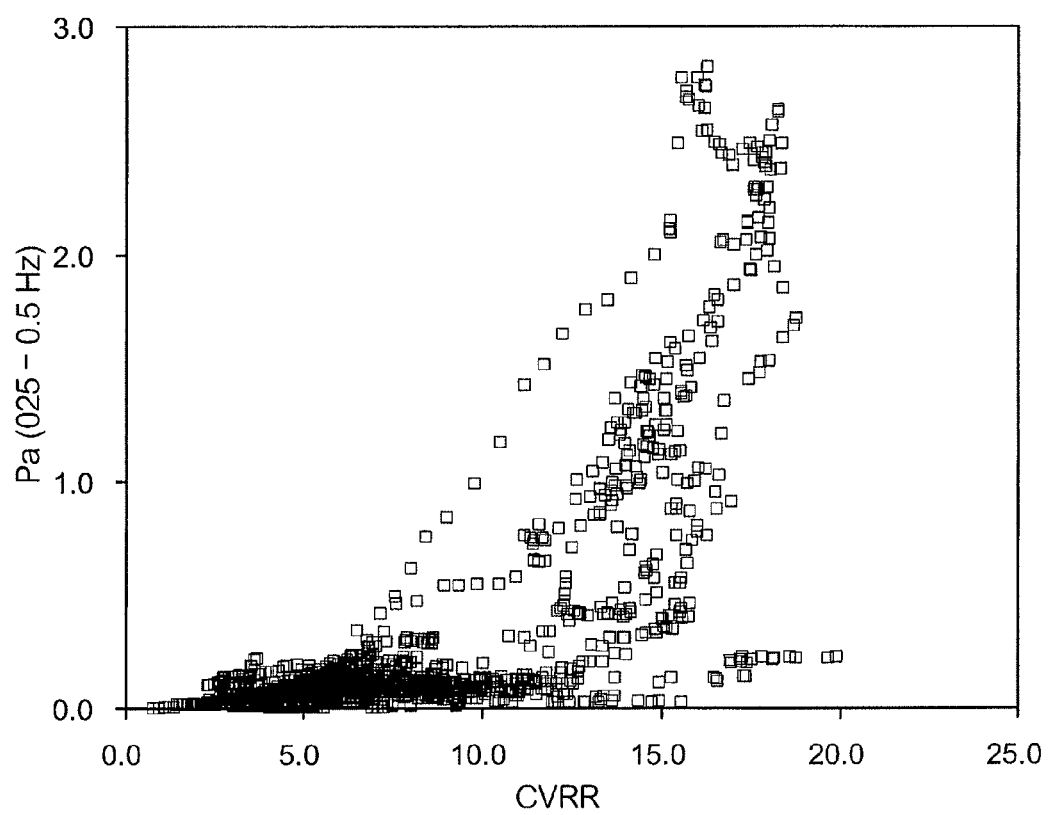
FIG. 14 is a diagram illustrating the relationship between the power and the variation coefficient.

FIG. 14 is a diagram illustrating the relationship between the power and the variation coefficient. The vertical axis indicates power [$msec^2$], and the horizontal axis indicates the variation coefficient CVRR [%]. As previously described, the values of the power and the variation coefficient when atrial fibrillation has developed are relatively high compared with those at the normal time. Accordingly, it is thought that the plot near the upper right in FIG. 14 corresponds to data measured when atrial fibrillation has developed. In the present embodiment, data is divided into two clusters using a clustering method, and the presence of atrial fibrillation is determined on the basis of the positional relationship of the two clusters in variation coefficient-power space.

Figure 15:
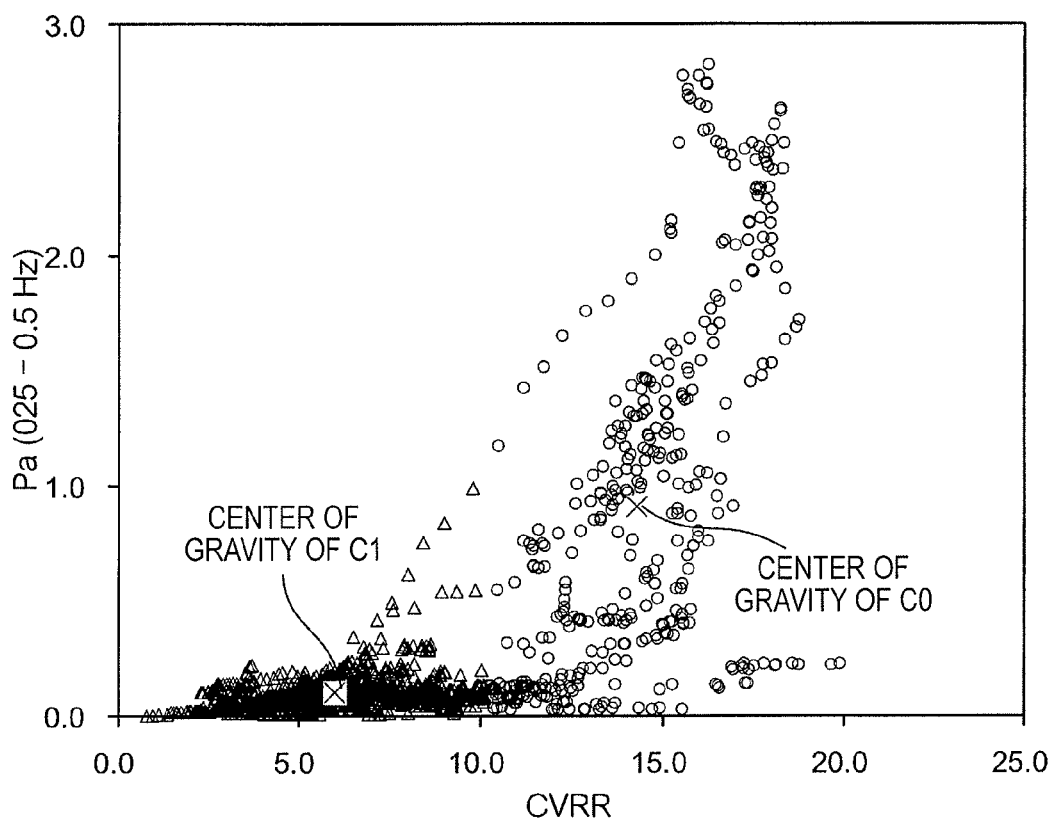
FIG. 15 is a diagram illustrating a result after clustering of data shown in FIG. 14.

FIG. 15 is a diagram illustrating a result after clustering of the data shown in FIG. 14. Thus, data is divided into two clusters using the clustering method (in this example, the k-means method). These two clusters are called a cluster C0 and cluster C1. The cluster C0 is a data group of relatively high variation coefficients and relatively high power, and the cluster C1 is a data group of relatively low variation coefficients and relatively low power. The data of the cluster C0 is expressed by a circle (O), and the cluster C1 is expressed by a triangle (Δ). In addition, according to the k-means method, the coordinates of the center of gravity of each cluster in the variation coefficient-power space are calculated. In FIG. 15, the positions of the centers of gravity of the clusters C0 and C1 are shown together.

FIG. 11 is referred to again. In step S503, the CPU 11 determines whether or not the position of the center of gravity of the cluster C0 is in a predetermined range, for example, a range of ±30% with the position of the center of gravity of the cluster C1 as a reference. When it is determined that the position of the center of gravity of the cluster C0 is outside the range of ±30% from the position of the center of gravity of the cluster C1 (step S503; NO), the CPU 11 proceeds to step S504. When it is determined that the position of the center of gravity of the cluster C0 is within the range of ±30% from the position of the center of gravity of the cluster C1 (step S503; YES), the CPU 11 proceeds to step S505.

In step S504, the CPU 11 determines that the cluster C0 is data when atrial fibrillation has developed.

When the position of the center of gravity of the cluster C0 is within the range of ±30% from the position of the center of gravity of the cluster C1, it is determined that the data cannot be divided into two clusters. In this case, as the possibility, a case where atrial fibrillation has not developed in the entire measurement period and a case where atrial fibrillation continues to develop in the entire measurement period can be considered. In these cases, the presence of atrial fibrillation is determined on the basis of the values of power and the variation coefficient. This process is performed from step S505.

In step S505, the CPU 11 calculates the coordinates (hereinafter, referred to as "average gravity center coordinates") of the average position (hereinafter, referred to as "average center of gravity") of the center of gravity of the cluster C0 and the center of gravity of the cluster C1. The average center of gravity is a simple average of the center of gravity of the cluster C0 and the center of gravity of the cluster C1 (that is, a midpoint of the center of gravity of the cluster C0 and the center of gravity of the cluster C1), for example. Alternatively, the average center of gravity may also be the weighted center (that is, the center of gravity of all measurement points) according to the number of data points of the center of gravity of the cluster C0 and the center of gravity of the cluster C1.

In step S506, the CPU 11 determines whether or not the average gravity center coordinates are in a predetermined range (for example, a variation coefficient of 10.0 or more and power of 0.5 or more). When it is determined that the average gravity center coordinates are in a predetermined range (step S506; YES), the CPU 11 determines that atrial fibrillation has developed in the entire measurement period (step S507). When it is determined that the average gravity center coordinates are not in a predetermined range (step S506; NO), the CPU 11 determines that atrial fibrillation has not developed in the entire measurement period (step S508).

FIG. 8 is referred to again. When it is determined that atrial fibrillation has not developed (step S410; NO), the CPU 11 returns to step S110 to continue the process. On the other hand, when it is determined that atrial fibrillation has developed (step S410; YES), the CPU 11 causes the display control unit 115 to display the determination result, which indicates that atrial fibrillation has developed, on the display unit 15 (step S420), and returns to step S110 to continue the process.

In addition, the CPU 11 may repeat the process of steps S110 to S140 regardless of the determination result in step S140. In this case, the CPU 11 may execute the process from step S210 in parallel with the process of steps S110 to S140 whenever the determination result in step S140 is YES. In this case, when the determination result in step S230 is NO or when the determination result in step S410 is NO, it is preferable to terminate the process from step S210 executed in parallel.

The above is an explanation of the atrial fibrillation determination process.

Figure 7:
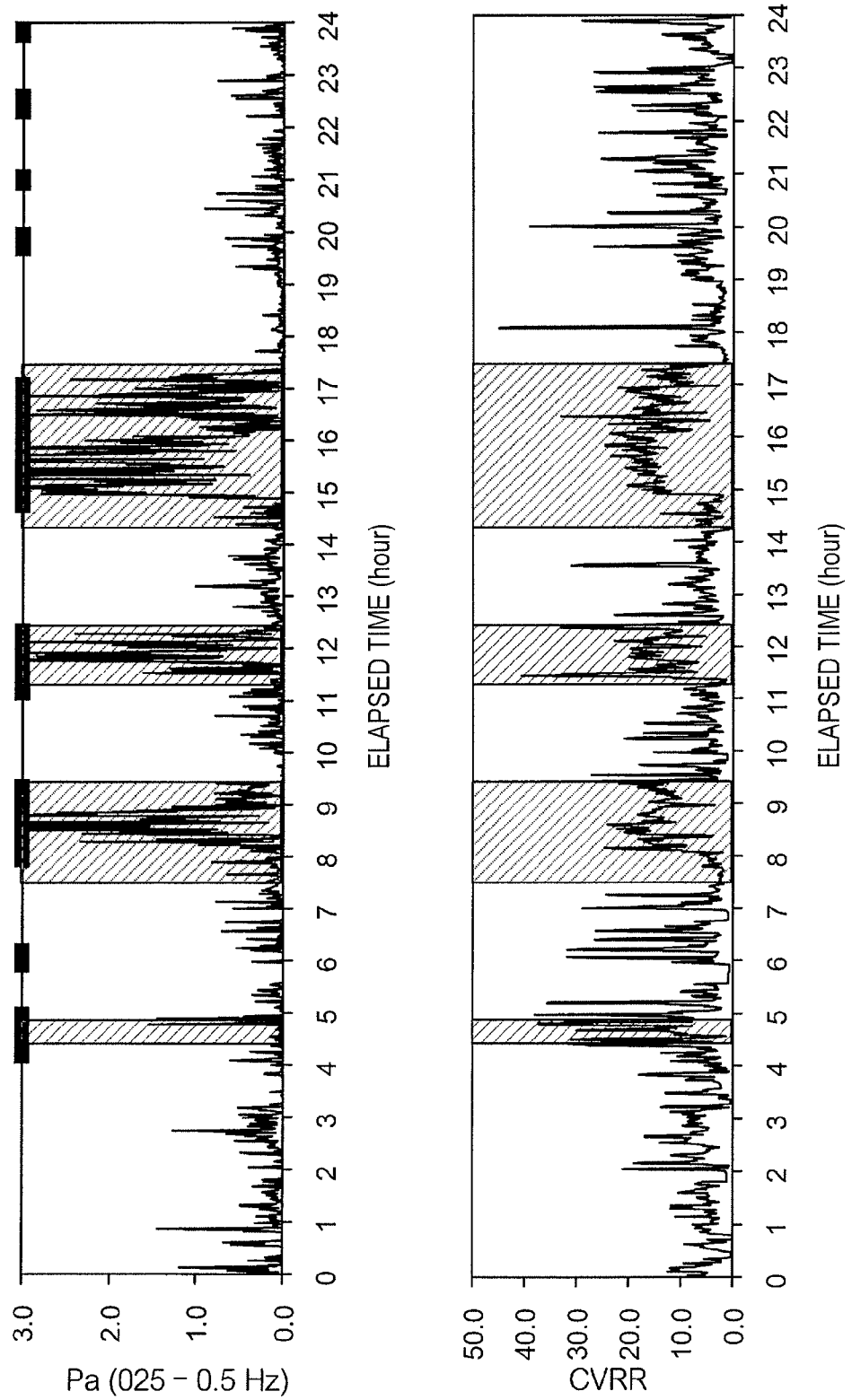
FIG. 7 is a diagram showing an analysis result in the embodiment.

FIG. 7 is a diagram showing a determination result in the present embodiment. FIG. 7 shows an analysis result of the signal shown in FIG. 12. A period determined that atrial fibrillation has developed by electrocardiogram analysis using a Holter monitor is shown together. In FIG. 8, a portion indicated by the thick line is a period determined that atrial fibrillation has developed in the present embodiment, and a hatched portion is a period determined that atrial fibrillation has developed by electrocardiogram analysis using the Holter monitor. For the period determined as where atrial fibrillation has developed by the Holter monitor, it is also determined that atrial fibrillation occurs with almost no exception in the present embodiment as well. In the present embodiment, some noise is detected as atrial fibrillation. However, for example, when determination as atrial fibrillation has been made in a period shorter than a predetermined threshold value, the determination result may be rejected (that is, when determination as atrial fibrillation has been continuously made in a period longer than the threshold value, the determination result indicating that atrial fibrillation has developed is adopted).

Thus, in the pulse wave measuring device 1 according to the embodiment of the invention, it is possible to determine atrial fibrillation while reducing the influence of body movement noise by measuring the average pulse wave RR interval instead of the pulse wave RR interval of each beat.

MODIFICATION EXAMPLES

While the embodiment of the invention has been described, the invention can be implemented in various ways as follows.

Modification Example 1

In the embodiment described above, the detected waveform signal L is a signal indicating the pulse wave detection result of the pulse wave detector 20. However, the detected waveform signal L may also be a waveform signal obtained as an electrocardiogram detection result. That is, the detected waveform signal L may be a waveform signal from which a parameter equivalent to the RR interval can be acquired.

Modification Example 2

In the embodiment described above, the noise reduction unit 111 is provided as a functional configuration of the atrial fibrillation analyzer 100. However, the noise reduction unit 111 does not necessarily need to be provided. In this case, the RR interval calculation unit 112 may acquire the detected waveform signal L for frequency analysis from the detected waveform signal storage region 121.

Modification Example 3

In the embodiment described above, the atrial fibrillation analyzer 100 is realized in the pulse wave measuring device 1. However, the atrial fibrillation analyzer 100 may also be realized in an information processing apparatus, such as a personal computer. In this case, the information processing apparatus may acquire the detected waveform signal L measured in advance from an external device and store the detected waveform signal L in the detected waveform signal storage region 121. Then, the information processing apparatus may determine the presence of atrial fibrillation by analyzing the detected waveform signal L by atrial fibrillation determination process.

Modification Example 4

In the embodiment described above, the device body 10 and the pulse wave detector 20 are connected to each other using the cable 30. However, the device body 10 and the pulse wave detector 20 may be wirelessly connected to each other. In this case, the device body 10 and the pulse wave detector 20 may exchange various signals, such as a control signal required for the control of the pulse wave detector 20 and the detected waveform signal L generated by the pulse wave detector 20, therebetween by wireless communication. In addition, each of the device body 10 and the pulse wave detector 20 may be made to have a configuration of a battery that can supply electric power thereto.

Modification Example 5

In the embodiment described above, the determination result of atrial fibrillation is displayed on the display unit 15 and is notified to the user. However, the analysis result of atrial fibrillation may also be notified by sound, vibration, or the like. For example, when the sound is used to notify the user of the atrial fibrillation analysis result, it is preferable to provide a speaker and a sound control unit that controls the content of sound output from the speaker on the basis of the information from the determination unit 114. For example, when the vibration is used to notify the user of the atrial fibrillation analysis result, it is preferable to provide a vibration actuator and a vibration control unit that controls the vibration content of the vibration actuator on the basis of the information from the determination unit 114. Thus, the display control unit 115 and the display unit 15 in the embodiment can also be conceptualized as a notification unit that notifies the user according to the determination result of atrial fibrillation.

Modification Example 6

Various parameters described in the embodiment, for example, the threshold value (±30%) of cluster separation, the predetermined range (variation coefficient of 10.0 or more and power of 0.5 or more) with respect to the average gravity center coordinates, the number of data points (20 points) of the movement averaging process, and the frame period (120 seconds) are examples, and the values of these parameters are not limited thereto. In addition, the algorithm of clustering is not limited to the k-means method. A data group constellation may be separated into two clusters by algorithms other than the k-means method. In addition, the specific method of determining the presence of atrial fibrillation is not limited to that described in FIG. 11. For example, the presence of atrial fibrillation may be determined by methods other than the method described in FIG. 11, such as comparing at least one of the power and the variation coefficient with a threshold value.

Modification Example 7

A control program in the embodiment described above can be provided in a state of being stored on a computer-readable recording medium, such as a magnetic recording medium (a magnetic tape, a magnetic disk, or the like), an optical recording medium (optical disc or the like), a magneto-optical recording medium, and a semiconductor memory. In addition, the pulse wave measuring device 1 may download each program through a network.

What is claimed is:

1. A pulse wave measuring device comprising:
an atrial fibrillation analyzer, comprising:
an acquisition unit that acquires a detected waveform signal indicating a detection result of a pulse wave or an electrocardiogram;
an RR interval calculation unit that calculates, on the basis of a spectrum of each unit period obtained by frequency analysis performed on the acquired detected waveform signal every unit period longer than 4 seconds and equal to or shorter than 16 seconds, a parameter corresponding to an average RR interval of the unit period every unit period;
a power calculation unit that calculates power of a frequency band determined in advance in an RR waveform signal indicating a temporal change of the average RR interval calculated by the RR interval calculation unit; and
an analysis unit that determines whether or not the power satisfies a specific condition and outputs information indicating presence of atrial fibrillation from the determination result; and
a notification unit coupled to the atrial fibrillation analyzer, wherein the notification unit outputs the information indicating the presence of atrial fibrillation via one or more of a display, a sound or a vibration.

2. The pulse wave measuring device according to claim 1, wherein the atrial fibrillation analyzer further comprises:
a variation coefficient calculation unit that calculates a variation coefficient of the average RR interval in the RR waveform signal,
wherein the analysis unit determines whether or not a set of the power and the variation coefficient satisfies the specific conditions and outputs information indicating presence of atrial fibrillation from the determination result.

3. The pulse wave measuring device according to claim 2, wherein the analysis unit divides a plurality of sets of the power and the variation coefficients, which are obtained in a plurality of unit periods, into a first cluster of relatively high power and relatively high variation coefficients and a second cluster of relatively low power and relatively low variation coefficients, and determines the presence of atrial fibrillation using conditions, which are based on positional relationship between a first center of gravity of the first cluster and a second center of gravity of the second cluster in variation coefficient-power space, as the specific conditions.

4. The pulse wave measuring device according to claim 3, wherein the specific conditions are conditions in which the first and second centers of gravity are separated from each other by a first threshold value, which is determined in advance, or more, and when it is determined that the specific conditions are satisfied, the analysis unit determines that the first cluster is in a state where atrial fibrillation has developed.

5. The pulse wave measuring device according to claim 4, wherein the specific conditions are conditions in which an average center of gravity of the first and second centers of gravity has power equal to or higher than a second threshold value determined in advance and a variation coefficient equal to or higher than a third threshold value determined in advance when the first and second centers of gravity are not separated from each other by the first threshold value or more, and when it is determined that the specific conditions are satisfied, the analysis unit determines that the first and second clusters are in a state where atrial fibrillation has developed.

6. The pulse wave measuring device according to claim 5, wherein the specific conditions are conditions in which the average center of gravity of the first and second centers of gravity does not have at least one of power equal to or higher than the second threshold value and a variation coefficient equal to or higher than the third threshold value when the first and second centers of gravity are not separated from each other by the first threshold value or more, and when it is determined that the specific conditions are satisfied, the analysis unit determines that the first and second clusters are in a state where atrial fibrillation has not developed.

7. The pulse wave measuring device according to claim 1, wherein a minimum frequency of the frequency band is equal to or greater than a reciprocal of the unit period.

8. The pulse wave measuring device according to claim 1, wherein a maximum frequency of the frequency band is equal to or less than ½ of a sampling frequency in the frequency analysis.

9. The pulse wave measuring device according to claim 1, further comprising:
a detection unit that detects the pulse wave or the electrocardiogram of a target person;

wherein the acquisition unit acquires a detected waveform signal obtained according to the detection result.

10. The pulse wave measuring device according to claim 9, wherein the acquisition unit includes a noise reduction unit that performs a filtering process for reducing a body movement noise component on the detected waveform signal and outputs the result as the detected waveform signal.

11. A non-transitory storage medium, storing a program causing a computer to execute:
acquiring, using a pulse wave measuring device, a detected waveform signal indicating a detection result of a pulse wave or an electrocardiogram;
calculating, using the pulse wave measuring device, on the basis of a spectrum of each unit period obtained by frequency analysis performed on the acquired detected waveform signal every unit period longer than 4 seconds and equal to or shorter than 16 seconds, a parameter corresponding to an average RR interval of the unit period every unit period;
calculating, using the pulse wave measuring device, power of a frequency band determined in advance in an RR waveform signal indicating a temporal change of the calculated average RR interval;
determining, using the pulse wave measuring device, whether or not the power satisfies a specific condition; and
outputting, on a notification unit of the pulse wave measuring device, information indicating presence of atrial fibrillation from the determination result.

12. A method of analyzing atrial fibrillation, comprising:
acquiring, using a pulse wave measuring device, a detected waveform signal indicating a detection result of a pulse wave or an electrocardiogram;
calculating, using the pulse wave measuring device, on the basis of a spectrum of each unit period obtained by frequency analysis performed on the acquired detected waveform signal every unit period longer than 4 seconds and equal to or shorter than 16 seconds, a parameter corresponding to an average RR interval of the unit period every unit period;
calculating, using the pulse wave measuring device, power of a frequency band determined in advance in an RR waveform signal indicating a temporal change of the calculated average RR interval;
determining, using the pulse wave measuring device, whether or not the power satisfies a specific condition; and
outputting, on a notification unit of the pulse wave measuring device, information indicating presence of atrial fibrillation from the determination result.

13. The pulse wave measuring device according to claim 1, wherein the notification unit is a display unit that displays the information indicating the presence of atrial fibrillation.

* * * * *